(12) United States Patent
Chiou et al.

(10) Patent No.: US 8,927,601 B2
(45) Date of Patent: Jan. 6, 2015

(54) USES OF N-BUTYLIDENEPHTHALIDE IN TREATING A LIVER INJURY AND IMPROVING LIVER FUNCTION

(75) Inventors: Tzyy-Wen Chiou, Hualien County (TW); Horng-Jyh Harn, Taipei (TW); Shinn-Zong Lin, Taichung (TW)

(73) Assignee: National Dong Hwa University, Huallen County (TW)

( * ) Notice: Subject to any disclaimer, the term of this patent is extended or adjusted under 35 U.S.C. 154(b) by 0 days.

(21) Appl. No.: 13/331,059

(22) Filed: Dec. 20, 2011

(65) Prior Publication Data

US 2013/0158108 A1 Jun. 20, 2013

(51) Int. Cl.
*A61K 31/343* (2006.01)

(52) U.S. Cl.
CPC .................................. *A61K 31/343* (2013.01)
USPC ....................................................... 514/470

(58) Field of Classification Search
None
See application file for complete search history.

(56) References Cited

U.S. PATENT DOCUMENTS

| 5,112,827 | A  | * | 5/1992 | Saunders et al. | ......... 514/263.36 |
| 2006/0110469 | A1 | * | 5/2006 | Luo et al. | ....................... 424/725 |
| 2009/0176873 | A1 | * | 7/2009 | Fowler et al. | ................. 514/470 |

FOREIGN PATENT DOCUMENTS

| CA | 3 615 200 A1 | 7/2009 |
| CN | 1430696 A | 7/2003 |
| CN | 1810241 | 8/2006 |
| CN | 101213436 A | 8/2009 |
| EP | 1 645 280 A1 | 4/2006 |
| EP | 2343051 | 7/2011 |
| TW | I317636 | 11/1992 |
| TW | 1298259 B | 7/2008 |
| TW | 201021801 A | 6/2010 |

OTHER PUBLICATIONS

"Virtual Evaluation on the Activities of Phthalides and Terpenoids from Angelica sinensis" by Yuan et al., Chin. Herb. Med. 2, 236-41 (2010).*
"Alcoholic Liver Disease" by Mailliard et al. in Harrison's Principles of Internal Medicine, 17th Ed., McGraw Hill (New York), pp. 1969-1970 (2008).*

Walter K A, et al.: Interstitial Taxol Delivered From a Biodegradable Polymer Implant Against Experimental Malignant Glioma, Cancer Research, American Association for Cancer Research, US, vol. 56, Apr. 15, 1994, pp. 2207-2212.
Tsai N-M, et al.: "The Antitumor Effects of Angelica Sinensis on Malignant Brain Tumors in Vitro and in Vivo", The Clinical Cancer Research, The American Association for Cancer Research, US, vol. 11, No. 9, May 1, 2005, pp. 3475-3484.
Lin, Yun-Lian, et al. "Inhibitory effects of ligusticum chuanxiong on the proliferation of rat hepatic stellate cells", Journal of Gastroenterology and Hepatology, vol. 28, Issue 8, pp. 1257-1265, 2006.
Yan, Ru, et al. "Pharmacokinetics and metabolism of ligustilide, a major bioactive component in Rhizoma Chuanxiong in the rat", Drug Metabolism and Disposition, vol. 36, Issue 2, pp. 400-408, 2008.
Lee, Ting-Fang, et al., "Studies on antiproliferative effects of phthalides from Ligusticum chuanxiong in hepatic stellate cells", Planta Medica, vol. 73, Issue 6, pp. 527, 534, 2007 (Abstract Only).
Chen, et al., "The induction of orphan nuclear receptor nur77 expression by n-butylenephthalide as pharmaceuticals on hepatocellular carcinoma cell therapy", Molecular Pharmacology, vol. 74, No. 4, Oct. 2001.
Lin, et al., "Inhibitory effects of Lingusticum chuanxiong on the proliferation of rat hepatic stellate cells", Journal of Gastroenterology and Hepatology, vol. 21, No. 8, Aug. 2006.
Lee, et al., "Studies on antiproliferative effects of phtalides from Lingusticum chuanziong in hepatic stellate cells", Planta Medica, vol. 73, No. 8, Jun. 2007 (Abstract Only).
Yan, et al., "Simultaneous quantification of 12 bioactive components of Lingusticum chuanziong Hort. By high-performance liquid chromatography", Journal of Pharmaceutical and Biomedical Analysis, New York, NY, US, vol. 37, No. 1, Feb. 2005.
Wang, et al, "Chemical composition and inhibitory effect on hepatic fibrosis of Danggui Buxue Decoction", Fltoterapia, vol. 81, May 2010.

* cited by examiner

*Primary Examiner* — Theodore R West
(74) *Attorney, Agent, or Firm* — Cesari and McKenna, LLP

(57) ABSTRACT

Provided is a method for treating a liver injury such as fibrosis, cirrhosis and hepatitis as well as a method for restoring liver function in a subject, which includes administrating to the subject a therapeutically effective amount of n-butylidenephthalide having the formula (I) as an active ingredient, or a pharmaceutically acceptable salt of ester thereof:

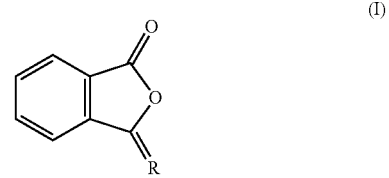

(I)

wherein R is $=CHCH_2CH_2CH_3$, and n-butylidenephthalide (I) is E form, Z form or a mixture thereof.

11 Claims, 10 Drawing Sheets

USES OF N-BUTYLIDENEPHTHALIDE IN TREATING A LIVER INJURY AND IMPROVING LIVER FUNCTION

BACKGROUND OF THE INVENTION

1. Field of the Invention

The present invention is related to novel uses of n-butylidenephthalide (abbreviated as n-BP hereinafter) in treating a liver injury such as liver fibrosis, liver cirrhosis or hepatitis, and in restoring/improving liver function after liver function adversely affected by a liver injury.

2. Descriptions of the Related Art

Liver fibrosis or more severe form, cirrhosis, is liver cells response to extrinsic injury from a variety of viral, toxin or metabolic insults. Cirrhosis is responsible for as many as 35 000 annual deaths in the United States, unless the progressive degeneration in liver function can be rescued with liver transplantation. Histologically, cirrhosis is characterized by excessive extracellular matrix deposition (i.e. fibrosis), which surrounds regenerative hepatocellular nodules.

In addition to deterioration in liver function, these nodules are also a seedbed for the formation of hepatocellular carcinoma. Clinically, Silymarin and Pentoxifylline (Trental) can significantly reduce the mortality of patients with alcoholic-induced liver cirrhosis. However, there is only ambiguous efficacy to attenuate liver fibrosis and improve liver function (Zhang et al., 2005)[1]. Therefore, effective medicines, foods or substances that can attenuate progression or induce regression of liver fibrosis are important.

*Angelica sinensis* (also known as Dong Quai) is indicated for menstrual disorders, including menopausal symptoms (Huntley and Ernst, 2003)[2]. It has also been widely used for conditions such as gastric mucosal damage, hepatic injury, impaired myocardial blood flow, and chronic glomerulonephritis (Yim et al., 2000, Ye et al., 2001a, Ye et al., 2001b)[3-5]. Furthermore, Dong Quai has been promoted in the United States for treatment of several gynecologic disorders (Abebe, 2002)[6].

Six major compounds have been isolated from *Angelica sinensis*: (E)-liguistilide, (Z)-liguistilide, n-butylidenephthalide, palmitic acid, b-sitosterol, and ferulic acid. n-butylidenephthalide (n-BP molecular weight, 188.22) and liguistilide (K2; molecular weight, 190.23) are particularly abundant (Wang et al., 1998)[7], with the former exhibiting more potency than ligustilide. In conscious rats, n-BP relieves angina without affecting blood pressure or the heart rate (Ko et al., 1998, Chan et al., 2009)[8-9]. Previously, we demonstrated that the acetone extract of *A. sinensis* inhibits the proliferation of cancer cells in vitro (Cheng et al., 2004)[10] and that the subsequently obtained chloroform extract of *A. sinensis* antagonizes brain tumor cells in vitro and in vivo (Tsai et al., 2006)[11]. We also demonstrated that the antitumor effects of n-BP on neuroblastoma, lung cancer, melanoma, teratoma, leukemia, breast cancer, and hepatocellular carcinoma in vitro and on GBM brain tumors both in vitro and in vivo. However, so far, there is no any study for n-BP against liver fibrosis or cirrhosis.

Liver fibrosis is the common consequence of different liver diseases characterized by chronic liver tissue damage. This process is a consequence of chronic activation of hepatic stellate cells (HSC), leading to cell proliferation and increased deposition of extracellular matrix components.

SUMMARY OF THE INVENTION

In this invention, based on serum oxaloacetate transaminase (GOT), glutamate pyruvate transaminase (GPT), bilirubin level and histology examination (Metavir score), we discover n-BP can inhibit liver inflammation. In addition, by using Metavir score on gross examination, hematoxylin and eosin staining and histochemical staining, we demonstrate n-BP can decrease liver collagen fiber and attenuate regeneration nodule leading to cured liver fibrosis. Finally, based on prothrombin time and serum albumin level which are indicators for liver function, our results indicate that n-BP can restore liver function after liver cells being injured.

DETAILED DESCRIPTION OF THE INVENTION

Figure 1A:
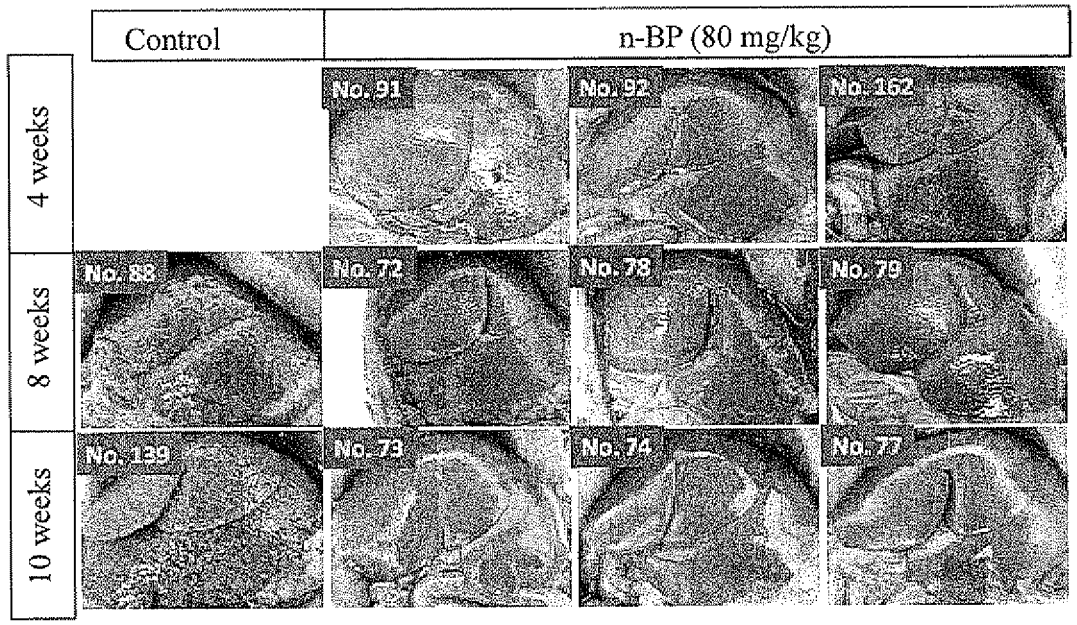
FIG. 1a: Gross finding of control group (olive oil oral administration) and 80 mg n-BP administration against TAA 200 mg/kg injection liver fibrosis. To induce the liver damage, for all experimental groups except the normal group, TAA 200 mg/kg injection were performed once every 3 days for 8 weeks. No. 91, No. 92 and No. 162 are photo-pictures of livers in experimental rats sacrificed after the TAA injection for 4 weeks. The therapy by oral administration at various BP concentrations or olive oil (as control) in the experimental groups started from the fifth week and ended at the end of week 8. No. 88 shows the liver of the group of olive oil administration at the end of week 8 (after 4 weeks' intake of olive oil). No. 72, No. 78 and No. 79 are livers of the group of 80 mg n-BP administration at the end of week 8. Two weeks after the therapy (at the end of week 10), the experimental rats were sacrificed; No. 73, No. 74 and No. 77 show livers of the group of 80 mg n-BP administration and No. 139 shows the liver of the group of olive oil administration.

Chronic liver diseases and hepatocirrhosis have been life-threatening. However, very few pharmaceuticals are available for their effective prevention or treatment. This invention provides a novel use of n-butylidenephthalide (n-BP) for inhibiting/treating liver fibrosis and hepatocirrhosis. In one aspect of the present invention a pharmaceutical composition for treating a liver injury and/or improving liver function in a subject is provided, which comprises a therapeutically effective amount of (n)-butylidenephthalide having the following formula (I) as an active ingredient, or a pharmaceutically acceptable salt or ester thereof

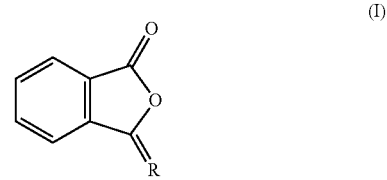

(I)

wherein R is $=CHCH_2CH_2CH_3$, and n-butylidenephthalide (I) is E form, Z form or a mixture thereof.

The pharmaceutical composition can be delivered orally, subcutaneously, intravenously, through dermal application or the forms of slow-release.

The present invention also provides a method for treating a liver injury in a subject comprising administering to the subject a therapeutically effective amount of (n)-butylidenephthalide having the following formula (I) as an active ingredient, or a pharmaceutically acceptable salt or ester thereof:

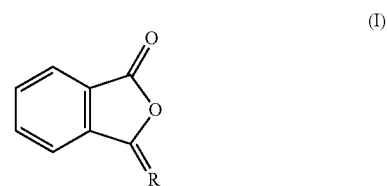

(I)

wherein R is $=CHCH_2CH_2CH_3$, and n-butylidenephthalide (I) is E form, Z form or a mixture thereof.

The present invention further provides a method for improving liver function in a subject comprising administering to the subject a therapeutically effective amount of (n)-butylidenephthalide having the aforesaid formula (I) as an active ingredient, or a pharmaceutically acceptable salt or ester thereof.

Preferably, the liver injury is liver fibrosis, liver cirrhosis or hepatitis.

Preferably, the liver function improved comprises a decrease in prothrombin time or an increase in serum albumin level.

Preferably, the therapeutically effective amount is about 8 mg to about 500 mg per kilogram of body weight per day.

Preferably, the active ingredient is synthesized, and alternatively it may be extracted and isolated from a plant. More preferably, the plant is *Angelica sinensis* or *Ligusticum chuanxiong*.

Preferably, the active ingredient is contained as a major ingredient in an extract of *Angelica sinensis* or *Ligusticum chuanxiong*.

Preferably, the active ingredient is administered to the subject orally, intravenously, intramuscularly, subcutaneously or in a slow release form.

Preferably, the liver injury is caused by chemical, microorganism, physical, alcoholic, viral or congenital biliary obstruction.

A thioacetamide-induced chronic liver damage rat model was used to demonstrate the feasibility of this invention. 5 ml/kg of thioacetamide (TAA) was injected intraperitoneally into Wistar rats every three days for eight weeks to induce the liver damage. The therapy was performed starting from the fifth week during the thioacetamide induction. 80 mg/Kg/day or 500 mg/Kg/day of n-BP were orally administered in experimental rats for four weeks. As compared with the control group (without therapy), the analysis of liver function index including GOT, GPT, albumin, total bilirubin and prothrombin time reveal significant recovery of liver damage in the n-BP therapy groups. Histopathological examinations show that, in the therapy groups, the inflammation and the accumulation of collagen fibers are significantly reduced. Based on these results, it is inferred that oral n-BP administration can facilitate the recovery of liver function from chronic liver damage and has the potential in the clinical application for treating liver fibrosis.

The detailed technology and preferred embodiments implemented for the subject invention are described in the following paragraphs accompanying the appended drawings for people skilled in this field to well appreciate the features of the claimed invention.

To Establish the Chronic Liver Fibrosis Model and Evaluate Liver Function

In this study, Wistar rats were obtained from LASCO CO., LTD (Taiwan). All procedures followed the ethical guidelines and were approved by the Institutional Animal Care and Use Committee of Dong-Hwa University, Taiwan.

To establish the chronic liver fibrosis model in rat, adult male Wistar rats (320±20 g) were used and were intraperitoneally injected with 200 mg/kg TAA (Sigma-Aldrich) once every 3 days for 8 weeks as the liver fibrosis model (78 rats). In the Normal group (24 rats), normal saline was used in place of the TAA. At the end of 4, 6, 8, and 10 weeks (i.e., day 28, 42, 56, and 70 respectively), these rats were sacrificed and cardiac blood samples were collected. These samples were analyzed with a biochemical analyzer (Integra 800; Roche, Holliston, Mass., USA) to measure the liver function index, which included glutamate oxaloacetate transaminase (GOT), glutamate pyruvate transaminase (GPT), serum albumin, total bilirubin and prothrombin time.

Afterwards, the histopathology of liver tissue samples obtained from the sacrificed rats were also analyzed. Liver tissue samples were fixed in 3.7% formaldehyde and then embedded in paraffin. Serial 3-μm sections of the embedded tissues were stained with hematoxylin and eosin or Masson's trichrome. Liver fibrosis is the excessive accumulation of collagen in liver, and therefore the accumulation of collagen is an important index for evaluating liver fibrosis. Masson's trichrome stain is frequently used to identify increases in collagenous tissue in fibrotic liver. For Masson's trichrome stain, sectioned samples were placed in Bouin's solution (Sigma-Aldrich) at 56° C. for 1 h and then were stained sequentially with the following solutions: Mayer's hematoxylin solution (Sigma-Aldrich) for 5 min, Biebrich scarlet-acid fuchsin solution (Sigma-Aldrich) for 15 min, phosphomolybdic acid-phosphotungstic acid (Sigma-Aldrich) for 15 min, and aniline blue (Sigma-Aldrich) for 5 min.

n-BP Oral Administration to Liver Fibrosis Model Experiment 78 rats with TAA induced fibrotic livers were randomly divided into 4 groups. For group 1 (TAA group), there were 24 rats which received no therapy. The remaining 58 were divided into three groups: Control group, n-BP treated group I (BP 80 mg/kg group) and n-BP treated group II (BP 500 mg/kg group). For these three groups, from the beginning of week 5 to the end of week 8, olive oil, n-BP (80 mg/Kg/day), and n-BP (500 mg/Kg/day) were orally administered once per day to the rats, wherein the dosage was 1 ml of olive oil per kilogram body weight (Control group), 1 ml of 80 mg/ml n-BP olive oil solution per kilogram body weight (BP 80 mg/kg group), and 1 ml of 500 mg/ml n-BP olive oil solution per kilogram of body weight (BP 500 mg/kg group), respectively. n-BP was purchased from Alfa Aesar®, cat. A10353.

Figure 2A:
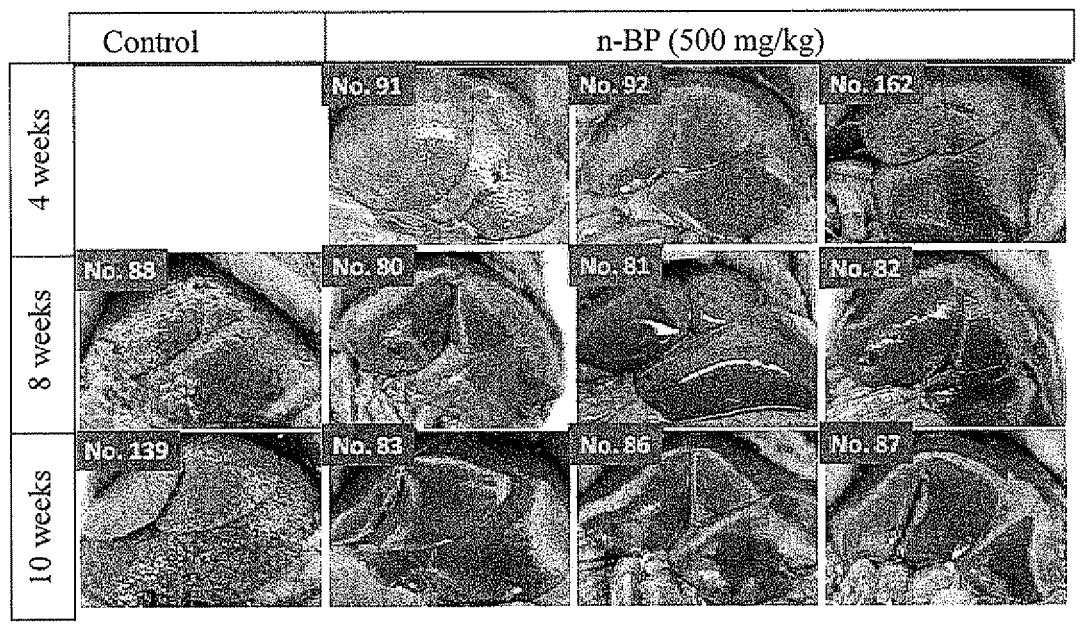
FIG. 2a: Gross finding of control group (olive oil oral administration) and 500 mg n-BP administration against TAA 200 mg/kg injection liver fibrosis. No. 91, No. 92 and No. 162 are photo-pictures of livers in experimental rats sacrificed after the TAA injection for 4 weeks. No. 88 shows the liver of the group of olive oil administration at the end of week 8 (after 4 weeks' intake of olive oil). No. 80, No. 81 and No. 82 are livers of the group of 500 mg n-BP administration at the end of week 8 (after 4 weeks' intake of 500 mg/Kg/day n-BP). No. 83, No. 86 and No 87 show livers of the group of 500 mg n-BP administration two weeks after the therapy (at the end of week 10) and No 139 shows that of the group of olive oil administration.

At the end of 6, 8, and 10 weeks, rats of each group were sacrificed and cardiac blood samples were collected. These samples were analyzed with a biochemical analyzer (Integra 800; Roche, Holliston, Mass., USA) to measure the liver function index, which included glutamate oxaloacetate transaminase (GOT), glutamate pyruvate transaminase (GPT), serum albumin, and prothrombin time. Afterwards, the histopathology of liver tissue samples obtained from the sacrificed rats was also analyzed. Liver tissue samples were fixed in 3.7% formaldehyde and then embedded in paraffin. Serial 3-μm sections of the embedded tissues were stained with hematoxylin and eosin or Masson's trichrome as described above.

n-BP Oral Administration Against TAA 200 mg/kg Injection Liver Fibrosis in Comparison with Control Group (Olive Oil) from Gross Examination, Hemotoxylin-Eosinophil Section and Masson's Trichrome Staining to Evaluate Efficacy of Attenuating Liver Fibrosis:

FIGS. 1*a* and 2*a* show the gross examination of the livers of rats in the Control group and therapy groups. One should observe the color, volume of the liver; whether exudation, thickening or conglutination exist; surface of liver is smooth or nodular. Normal liver is brown red color with smooth surface, as we can see that No. 73 and No. 78 in FIG. 1*a* (the BP 80 mg/kg group) and No. 81 and No. 87 in FIG. 2*a* (the BP 500 mg/kg group) become even better like normal liver morphology. Liver enlarges with granular surface and stiff texture, if it got injured, just like the Control group (FIG. 1*a*, 2*a*: No. 88, 139).

Figure 1B:
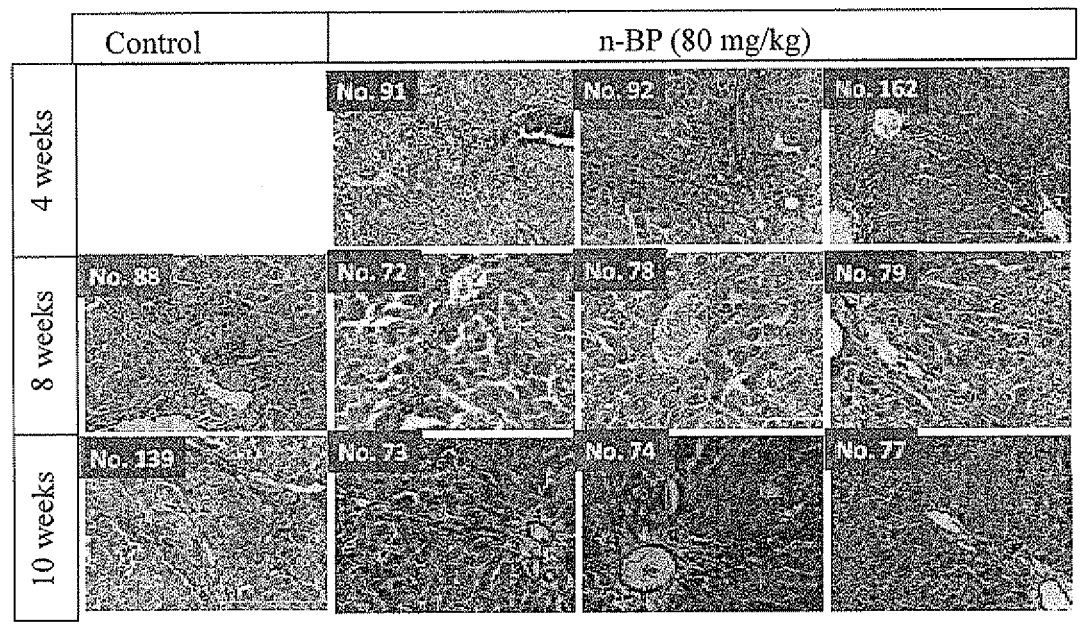
FIG. 1b: Hematoxylin and eosin staining of rat liver sections on control group (olive oil oral administration) and 80 mg n-BP administration against TAA 200 mg/kg injection liver fibrosis. No. 88 shows the liver section of the group of olive oil administration at the end of week 8 (after 4 weeks' intake of olive oil). No. 72, No. 78 and No. 79 are liver-sections of the group of 80 mg n-BP administration at the end of week 8. Two weeks after the therapy (at the end of week 10), the experimental rats were sacrificed; No. 73, No. 74 and No. 77 show liver-sections of the group of 80 mg n-BP administration and No. 139 shows the liver-section of the group of olive oil administration.
Figure 2B:
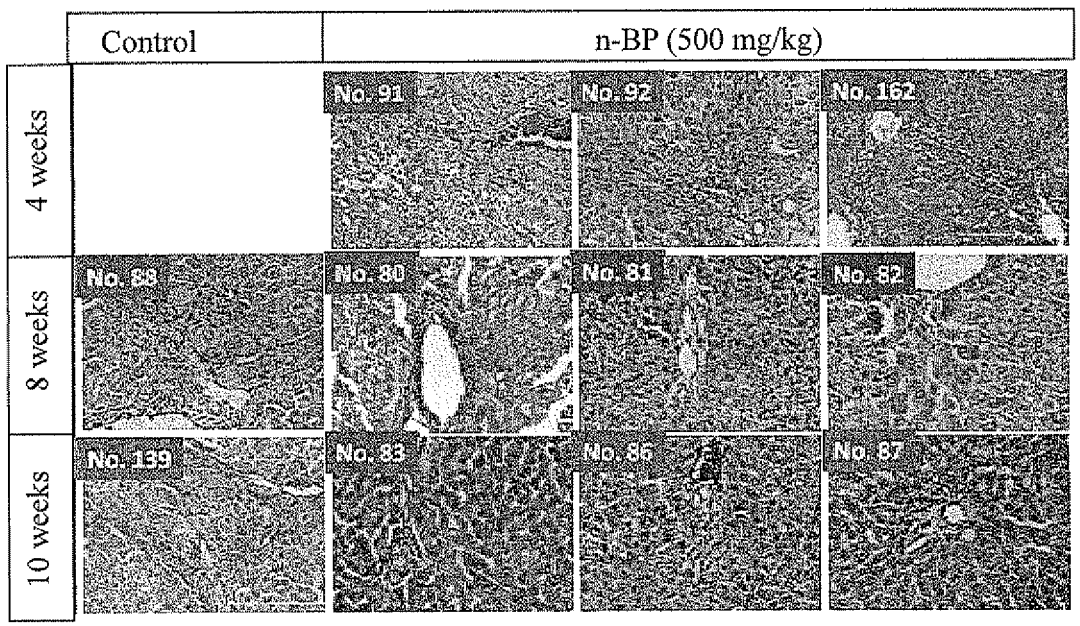
FIG. 2b: Hematoxylin and eosin staining of rat liver sections on control group (olive oil oral administration) and 500 mg n-BP administration against TAA 200 mg/kg injection liver fibrosis. No. 91, No. 92 and No. 162 are photo-pictures of liver-sections in experimental rats sacrificed after the TAA injection for 4 weeks. No. 88 shows the liver-section of the group of olive oil administration at the end of week 8 (after 4 weeks' intake of olive oil). No. 80, No. 81 and No. 82 are liver-sections of the group of 500 mg n-BP administration at the end of week 8 (after 4 weeks' intake of 500 mg/Kg/day n-BP). No. 83, No. 86 and No. 87 show liver-sections of the group of 500 mg n-BP administration two weeks after the therapy (at the end of week 10) and No. 139 shows that of the group of olive oil administration.

Hematoxylin and eosin staining of damaged rat liver tissue sections indicate that tissue vacuolation, necrosis and the degeneration of cell nuclei were observed in the liver sections from thioacetamide-induced liver fibrosis rats of the control group (FIG. 1*b*, 2*b*: No. 88, 139). Histopathologic data also suggest that n-BP administration ameliorates liver damage; recovery from tissue degeneration and vacuolation was evident in the n-BP groups at the end of 8 weeks and 10 weeks (FIG. 1*b*: No. 72, 78, 79, 73, 74, 77 and FIG. 2*b*: No. 80, 81, 82, 83, 86, 87), whereas the control group (olive oil) still show serious inflammation and necrosis (FIG. 1*b*, 2*b*: No. 88, 139).

Figure 1C:
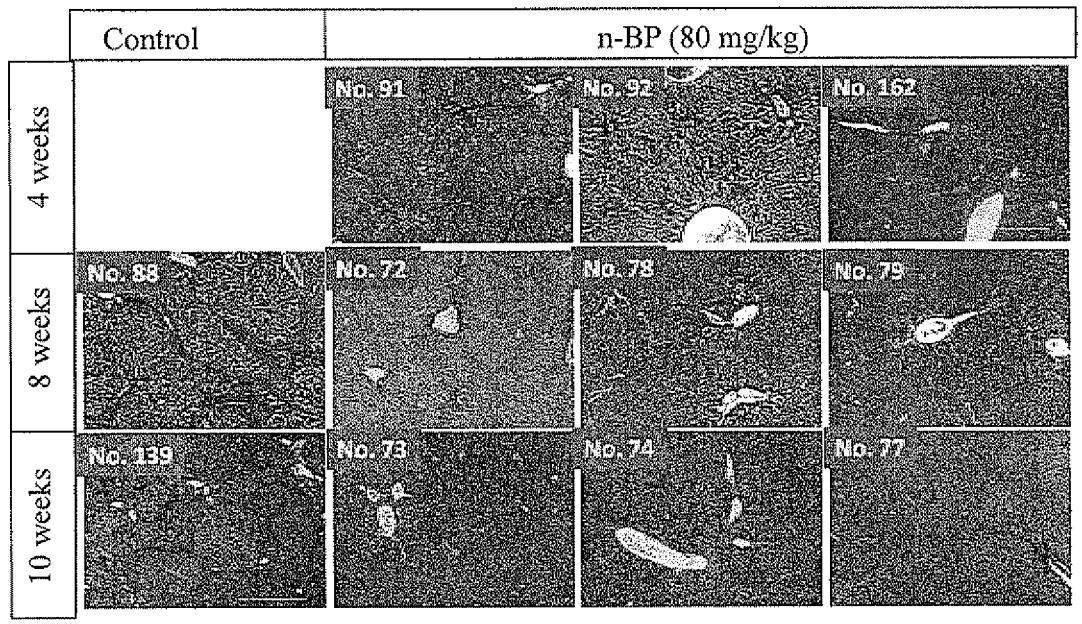
FIG. 1c: Masson's Trichrome staining of rat liver sections on control group (olive oil oral administration) and 80 mg n-BP administration against TAA 200 mg/kg injection liver fibrosis. No. 88 shows the liver section of the group of olive oil administration at the end of week 8 (after 4 weeks' intake of olive oil). No. 72, No. 78 and No. 79 are liver-sections of the group of 80 mg n-BP administration at the end of week 8. Two weeks after the therapy (at the end of week 10), the experimental rats were sacrificed; No. 73, No. 74 and No. 77 show liver-sections of the group of 80 mg n-BP administration and No. 139 shows the liver-section of the group of olive oil administration.
Figure 2C:
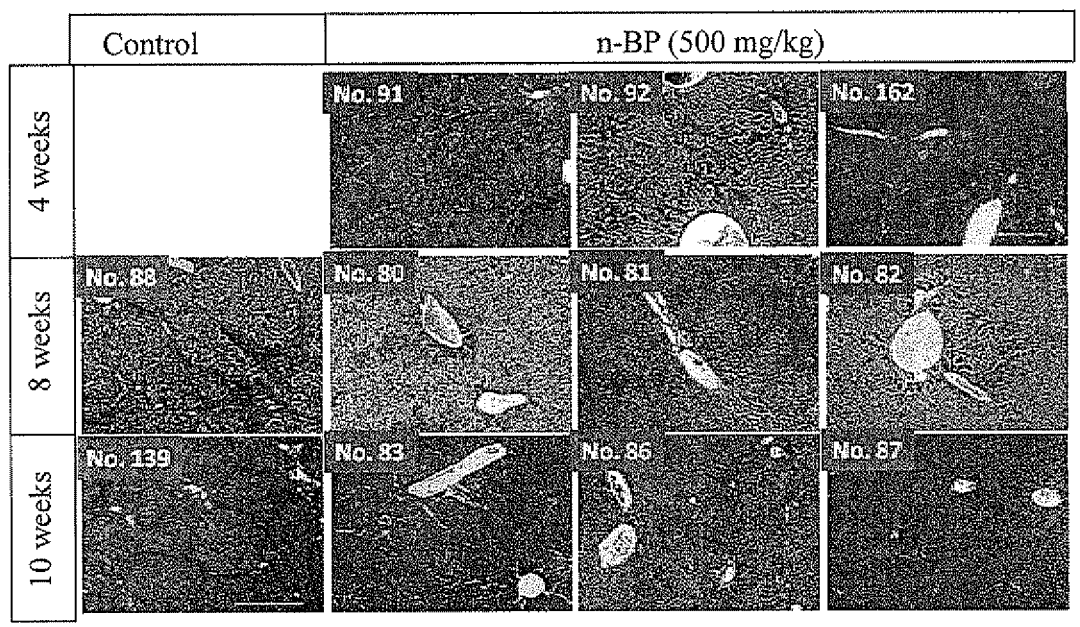
FIG. 2c: Mason Trichrome staining of rat liver sections on control group (olive oil oral administration) and 500 mg n-BP administration against TAA 200 mg/kg injection liver fibrosis. No. 91, No. 92 and No. 162 are photo-pictures of liver-sections in experimental rats sacrificed after the TAA injection for 4 weeks. No. 88 shows the liver-section of the group of olive oil administration at the end of week 8 (after 4 weeks' intake of olive oil). No. 80, No. 81 and No. 82 are liver-sections of the group of 500 mg n-BP administration at the end of week 8 (after 4 weeks' intake of 500 mg/Kg/day n-BP). No. 83, No. 86 and No. 87 show liver-sections of the group of 500 mg n-BP administration two weeks after the therapy (at the end of week 10) and No. 139 shows that of the group of olive oil administration.

Masson's trichrome staining reveals severe accumulation of collagen in livers from the liver fibrosis rats. Collagen degradation was found at day 8 weeks (FIG. 1*c*: No. 72, 78, 79; FIG. 2*c*: No. 80, 81, 82) and 10 week in the n-BP treated groups (FIG. 1c: No. 73, 74, 77; FIG. 2c: No. 83, 86, 87), whereas the control group still shows substantial collagen accumulation (FIG. 1c, FIG. 2c: No. 88, 139).

Figure 3:
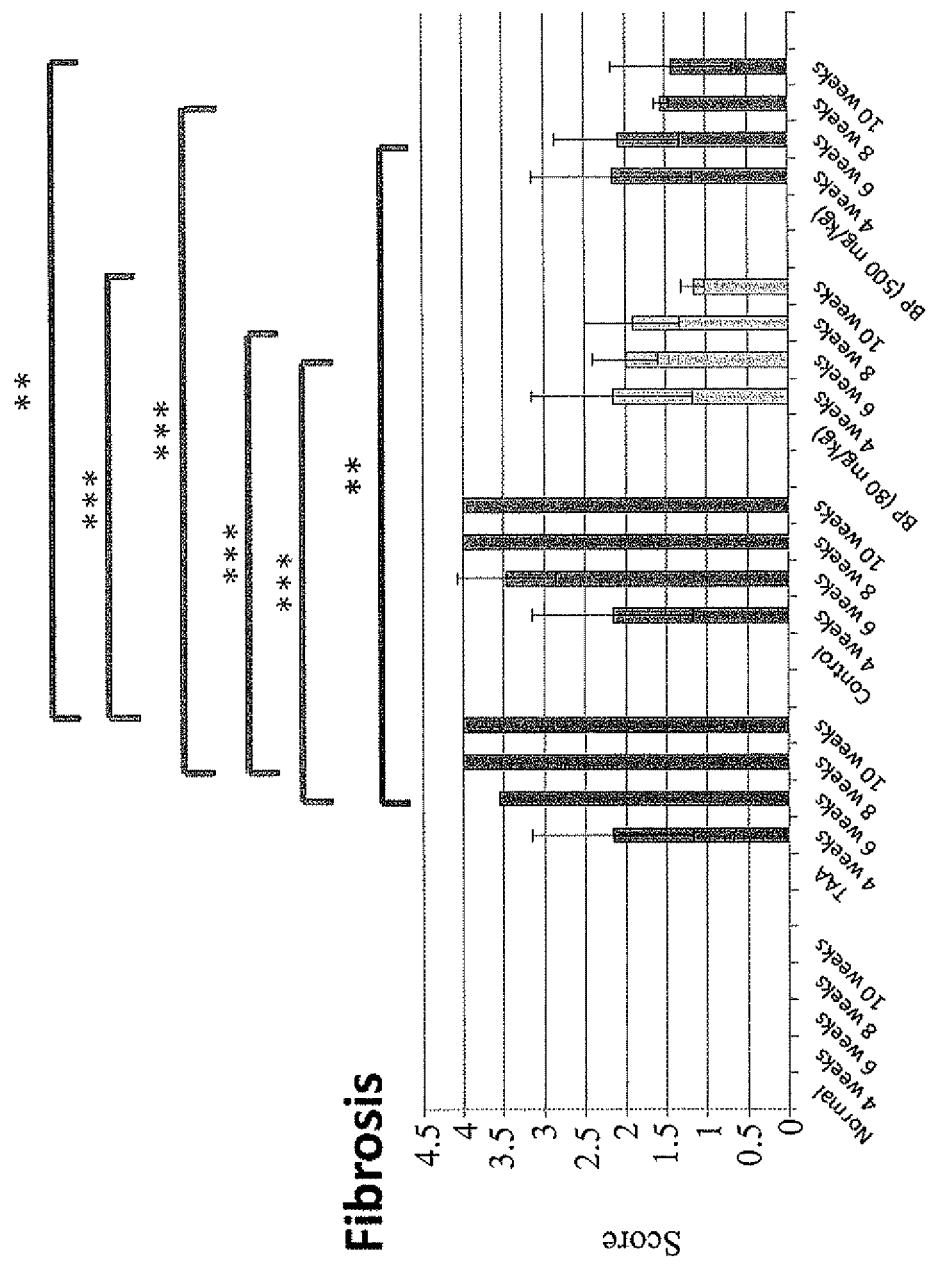
FIG. 3: The quantity score of liver fibrosis (according to Metavir scoring system) at 4 weeks, 6 weeks, 8 weeks and 10 weeks in each experimental group: Normal, TAA induction, olive oil, BP (80 mg/kg) and BP (500 mg/kg). All data were shown as mean with SD. For the comparison of different treatments in two groups, the data were analyzed by using the Student's t-test. Values of $p<0.05$ are considered significant (*), $p<0.01$ are considered highly significant (), and $p<0.001$ are considered extremely significant (*).

The fibrosis score that was generated by using fibrosis grade (Table 1) is lower in the n-BP treated groups than in the control group 42, 56 and 70 days (FIG. 3). Masson's trichrome staining for collagen shows almost no collagen accumulation in the n-BP treated groups on 42, 56 and 70 days (fibrosis grade 1-2) (FIG. 3), whereas the control group still shows a significant amount of collagen accumulation on 42, 56 and 70 days (fibrosis grade 3-4) (FIG. 3).

Figure 4:
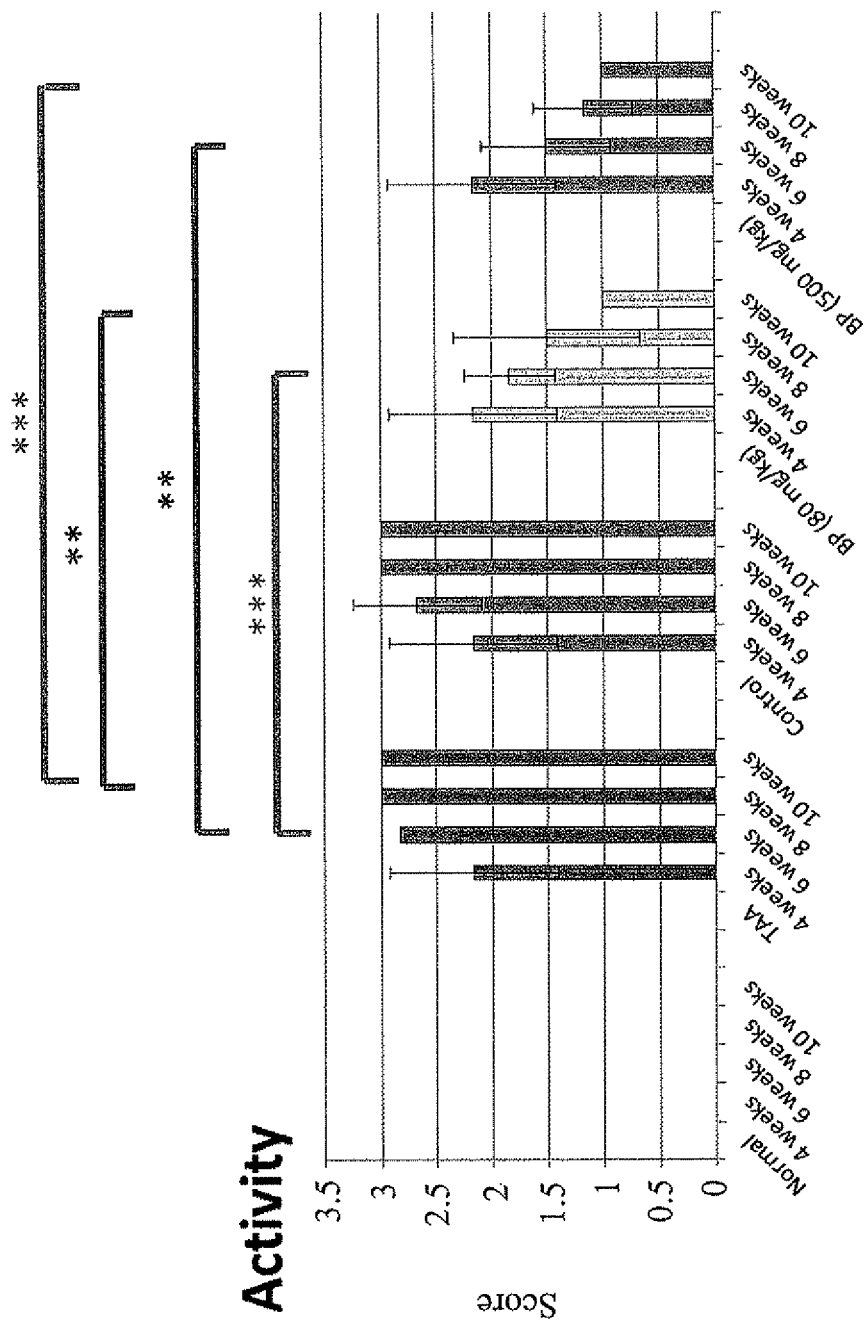
FIG. 4: The quantity score of liver activity according to Metavir scoring system at 4 weeks, 6 weeks, 8 weeks and 10 weeks in each experimental group: Normal, TAA induction, Olive oil, BP (80 mg/kg) and BP (500 mg/kg). All data were shown as mean with SD. For the comparison of different treatments in two groups, the data were analyzed by using the Student's t-test.

The inflammatory activity scores (Table 1) were examined (FIG. 4). These findings suggested that an improvement in the recovery of the damaged liver occurs 2 weeks after n-BP treatment.

TABLE 1

METAVIR scoring for liver fibrosis (F) and inflammatory activity (A)

| Score | Description |
| --- | --- |
| F0 | No fibrosis |
| F1 | Portal fibrosis without septa |
| F2 | Portal fibrosis with few septa |
| F3 | Numerous septa without cirrhosis |
| F4 | Cirrhosis |
| A0 | No activity |
| A1 | Mild activity |
| A2 | Moderate activity |
| A3 | Severe activity | n-BP Oral Administration Against TAA 200 mg/kg Injection Liver Fibrosis in Comparison with Control Group (Olive Oil) from SGOT, SGPT, Bilirubin to Evaluate Efficacy of Attenuate Liver Inflammatory Activity.

Figure 5A:
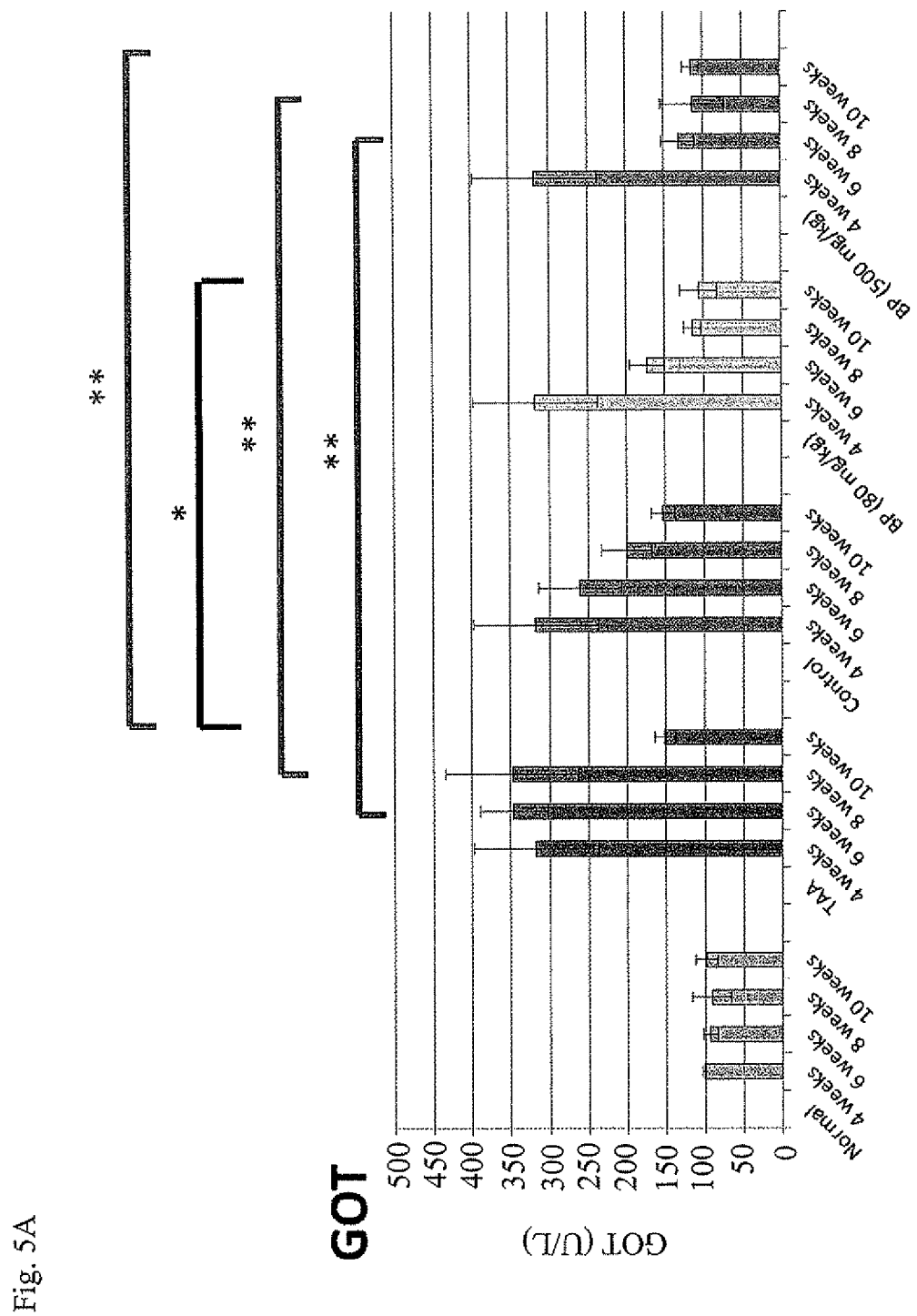
FIG. 5A: Plasma biochemical value of serum GOT at 4 weeks, 6 weeks, 8 weeks and 10 weeks in each experimental group: Normal, TAA induction, Olive oil, BP (80 mg/kg) and Bp (500 mg/kg). All data were shown as mean with SD. For the comparison of different treatments in two groups, the data were analyzed by using the Student's t-test.
Figure 5B:
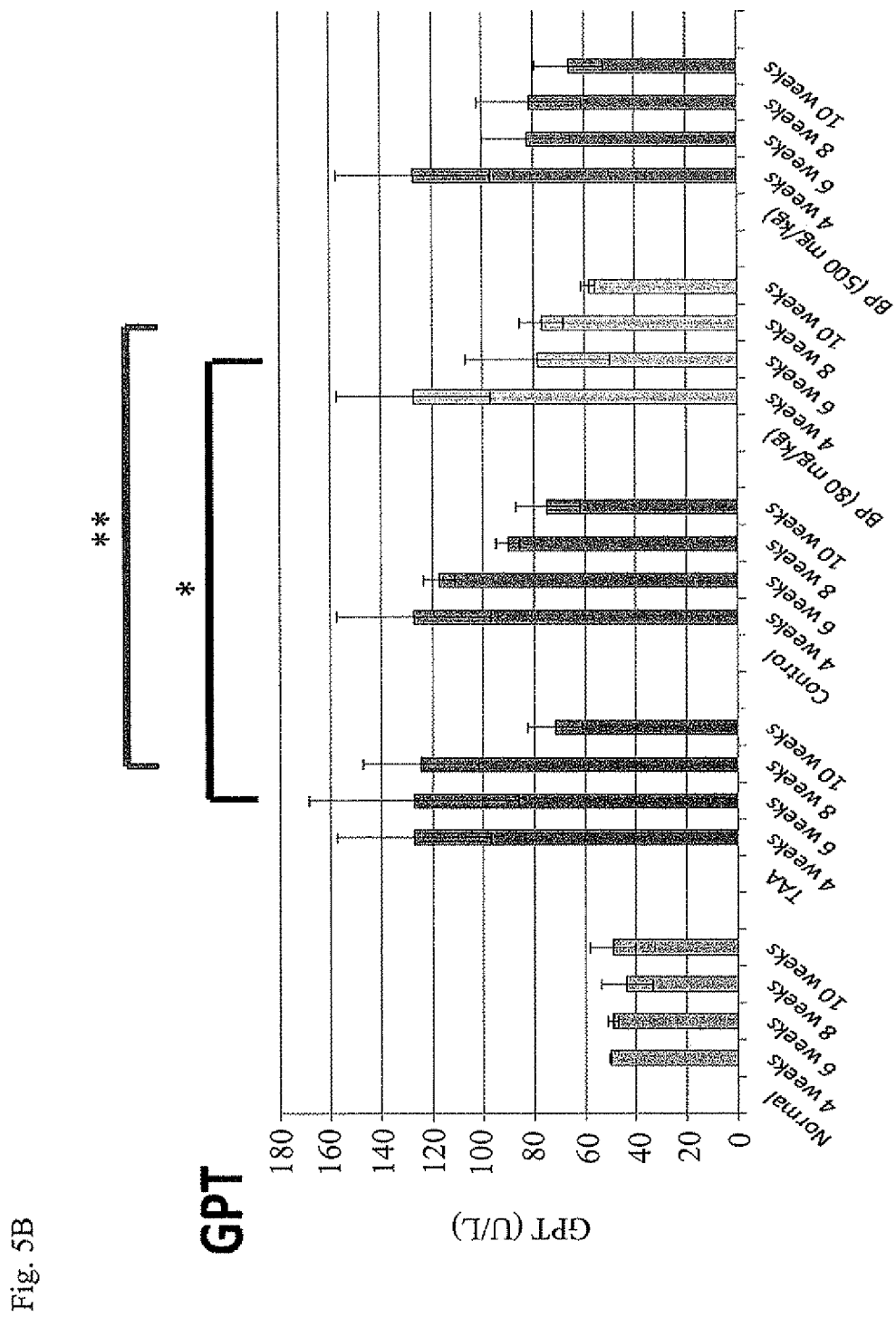
FIG. 5B: Plasma biochemical value of serum GPT at 4 weeks, 6 weeks, 8 weeks and 10 weeks in each experimental group: Normal, TAA induction, Olive oil, BP (80 mg/kg) and Bp (500 mg/kg). All data were shown as mean with SD. For the comparison of different treatments in two groups, the data were analyzed by using the Student's t-test.
Figure 6:
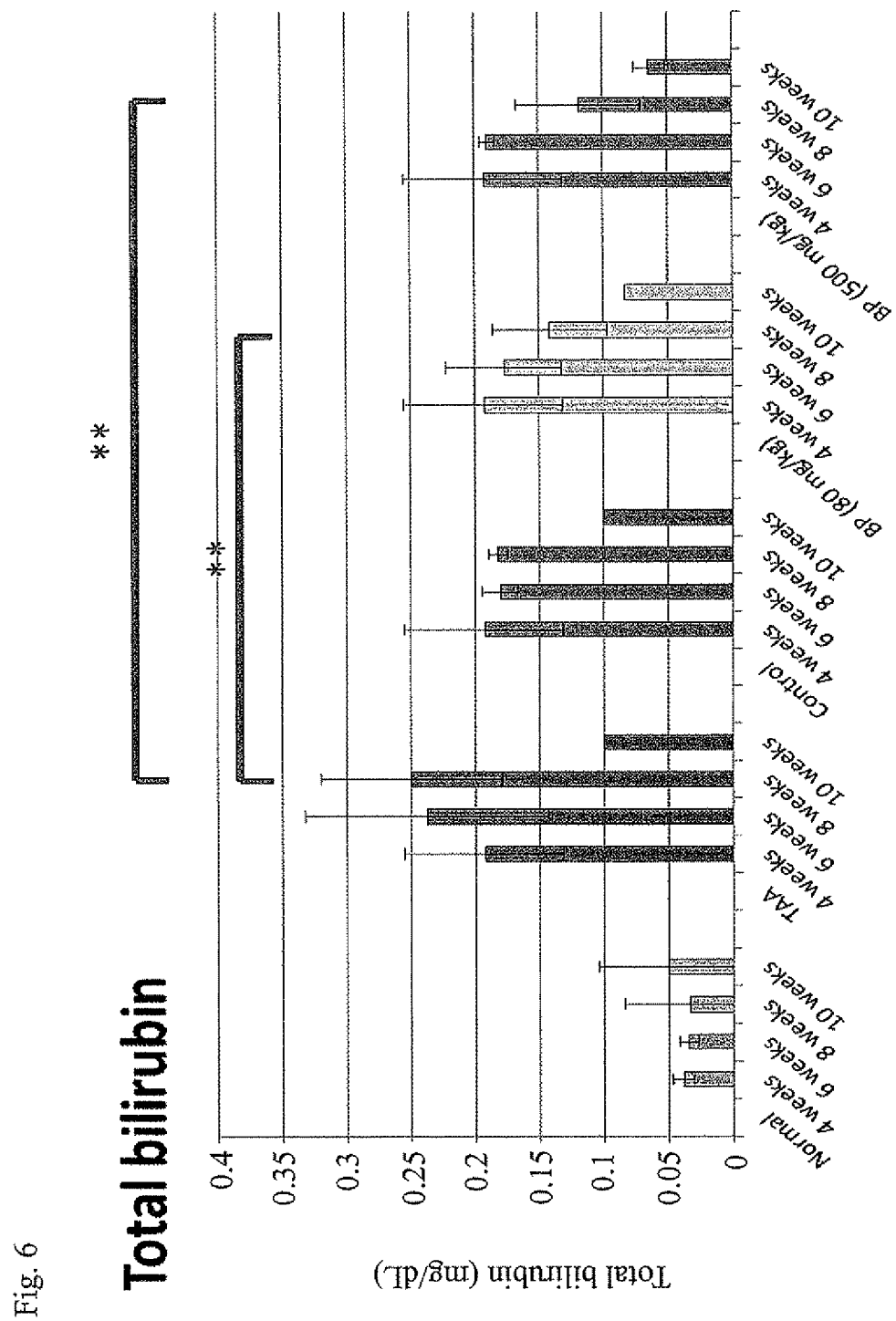
FIG. 6: Plasma biochemical value of total bilirubin at 4 weeks, 6 weeks, 8 weeks and 10 weeks in each experimental group: Normal, TAA induction, Olive oil, BP (80 mg/kg) and Bp (500 mg/kg). All data were shown as mean with SD. For the comparison of different treatments in two groups, the data were analyzed by using the Student's t-test.

In the liver fibrosis rat groups, serum GOT, GPT and total bilirubin levels, compared to the Normal group, are sharply increased at the end of week 4 (prior to treatments), indicating liver damage (FIG. 5A, FIG. 5B and FIG. 6).

In both the n-BP treated groups, GOT and GPT levels decline to near-normal values at the end of week 10, while in the Control group they still remain significantly higher than those of the Normal group (FIG. 5A, and FIG. 5B). As shown in FIG. 6, the serum total bilirubin levels in both the n-BP treated groups decline at the end of week 6 (two weeks after treatments) and continuously to decline to the end of week 10, while the serum total bilirubin level in the control group does not show declining until the end of week 8. At the end of week 10 the serum total bilirubin levels in both the n-BP treated groups are significantly lower than that of the Control group. The oral intake of n-BP can attenuate liver inflammatory activity in view of these data.

n-BP Oral Administration Against TAA 200 mg/kg Injection Liver Fibrosis in Comparison with Control Group (Olive Oil) from Albumin Level and Prothrombin Time to Evaluate Efficacy of Restoring Liver Function.

Figure 7:
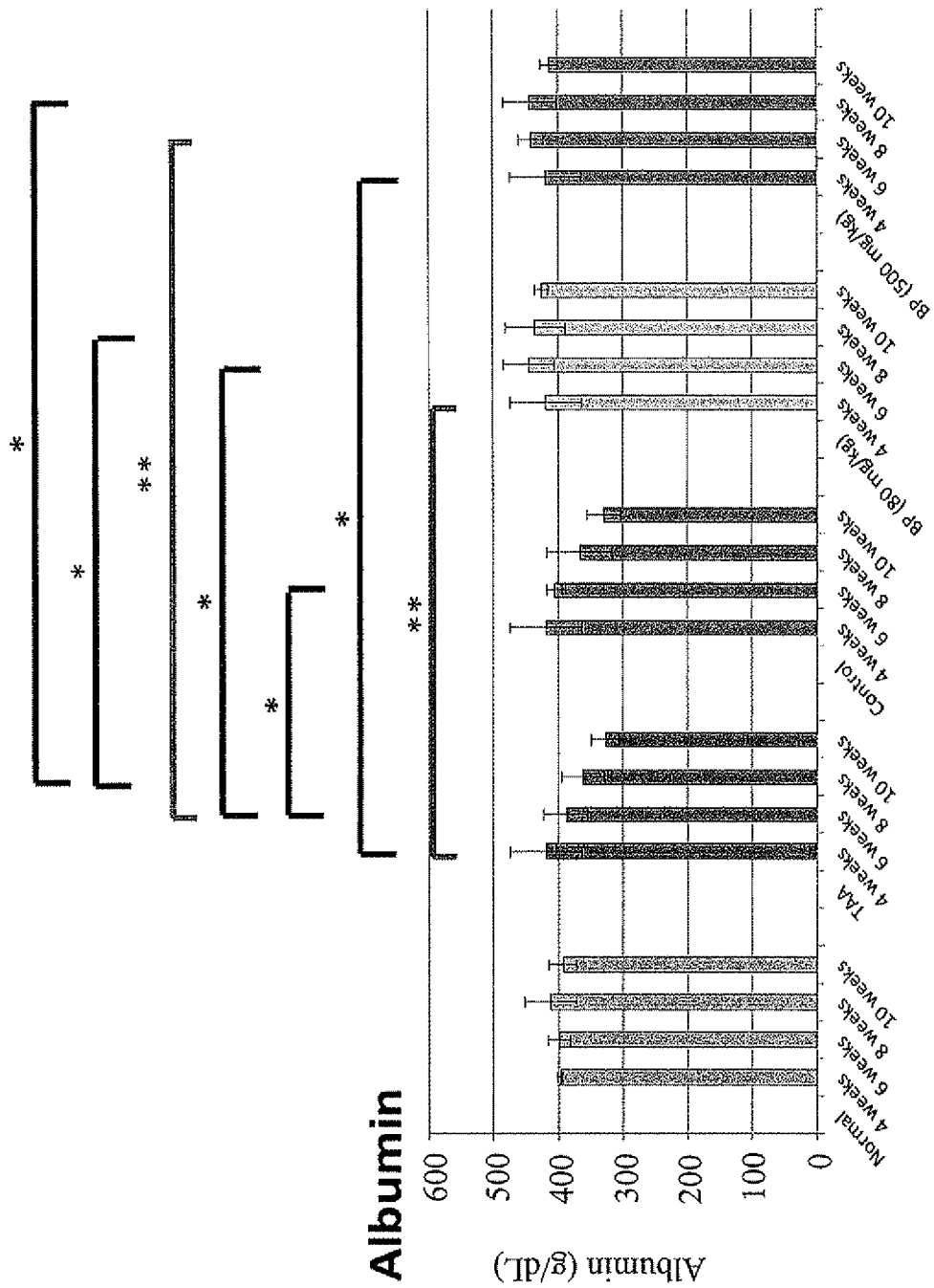
FIG. 7: Plasma biochemical value of serum albumin at 4 weeks, 6 weeks, 8 weeks and 10 weeks in each experimental group: Normal, TAA induction, Olive oil, BP (80 mg/kg) and Bp (500 mg/kg). All data were shown as mean with SD. For the comparison of different treatments in two groups, the data were analyzed by using the Student's t-test.
Figure 8:
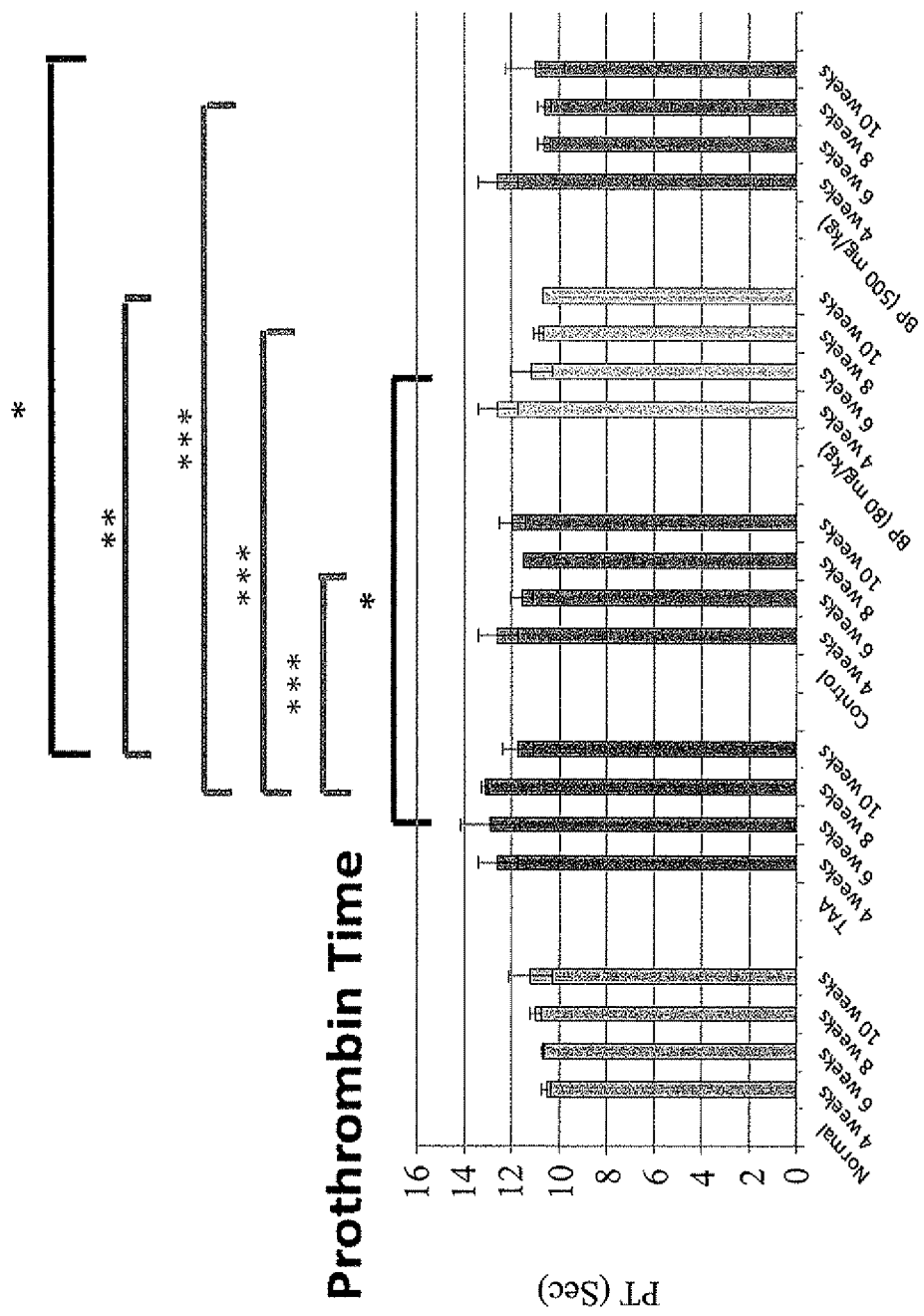
FIG. 8: Plasma biochemical value of prothrombin time at 4 weeks, 6 weeks, 8 weeks and 10 weeks in each experimental group: Normal, TAA induction, Olive oil, BP (80 mg/kg) and Bp (500 mg/kg). All data were shown as mean with SD. For the comparison of different treatments in two groups, the data were analyzed by using the Student's t-test.

From the beginning of the TAA injection to the end of 8 weeks, the TAA-induced liver damage decreases albumin (from 4.04±0.27 to 3.62±0.33 g/dl) and significantly increases prothrombin time (from 10.9±0.32 to 12.6±0.78 s) in the blood of the TAA group, as shown in FIGS. 7 and 8. The biochemical results in these experiments are consistent with previous reports (Zhao et al., 2005, Abdel Aziz et al., 2007, Dai et al., 2009, Lin et al., 2010)[12-15], suggesting significantly reduced liver function in these experimental rats.

The albumin level rises in the n-BP treated groups at the ends of week 6 and week 8 (two and four weeks after treatments); however, the Control group shows the opposite, as shown in FIG. 7. Serum albumin levels in the n-BP treated groups have been recovered to a greater extent than in the Control group (3.62±0.33 vs. 4.35±0.47) at the end of week 10. The prothrombin time in the Control group and in both the n-BP treated groups decreases from the end of week 6. The prothrombin time at the end of week 10 in both the n-BP treated groups is decreased to approach that of the Normal group; however, the Control group still have a longer prothrombin time in comparison with that in the Normal group, as shown in FIG. 8.

The restorations of prothrombin time and serum albumin levels suggest that 2 or 3 weeks after the n-BP treatment, functional liver mass is regenerated.

REFERENCES

[1] Zhang F K, Zhang J Y, Jia J D (2005) Treatment of patients with alcoholic liver disease. Hepatobiliary Pancreat Dis Int 4:12-17.

[2] Huntley A L, Ernst E (2003) A systematic review of herbal medicinal products for the treatment of menopausal symptoms. Menopause 10:465-476.

[3] Yim T K, Wu W K, Pak W F, Mak D H, Liang S M, Ko K M (2000) Myocardial protection against ischaemia-reperfusion injury by a Polygonum multiflorum extract supplemented 'Dang-Gui decoction for enriching blood', a compound formulation, ex vivo. Phytother Res 14:195-199.

[4] Ye Y N, Koo M W, Li Y, Matsui H, Cho C H (2001a) *Angelica sinensis* modulates migration and proliferation of gastric epithelial cells. Life Sci 68:961-968.

[5] Ye Y N, Liu E S, Li Y, So H L, Cho C C, Sheng H P, Lee S S, Cho C H (2001b) Protective effect of polysaccharides-enriched fraction from *Angelica sinensis* on hepatic injury. Life Sci 69:637-646.

[6] Abebe W (2002) Herbal medication: potential for adverse interactions with analgesic drugs. J Clin Pharm Ther 27:391-401.

[7] Wang H, Chen R, Xu H (1998) [Chemical constituents of radix *Angelicae Sinensis*]. Zhongguo Zhong Yao Za Zhi 23:167-168, inside backcover.

[8] Ko W C, Sheu J R, Tzeng S H, Chen C M (1998) The selective antianginal effect without changing blood pressure of butylidenephthalide in conscious rats. Planta Med 64:229-232.

[9] Chan S S, Jones R L, Lin G (2009) Synergistic interaction between the *Ligusticum* chuanxiong constituent butylidenephthalide and the nitric oxide donor sodium nitroprusside in relaxing rat isolated aorta. J Ethnopharmacol 122: 308-312.

[10] Cheng Y L, Chang W L, Lee S C, Liu Y G, Chen C J, Lin S Z, Tsai N M, Yu D S, Yen C Y, Ham H J (2004) Acetone extract of *Angelica sinensis* inhibits proliferation of human cancer cells via inducing cell cycle arrest and apoptosis. Life Sci 75:1579-1594.

[11] Tsai N M, Chen Y L, Lee C C, Lin P C, Cheng Y L, Chang W L, Lin S Z, Ham H J (2006) The natural compound n-butylidenephthalide derived from *Angelica sinensis* inhibits malignant brain tumor growth in vitro and in vivo. J Neurochem 99:1251-1262.

[12] Zhao D C, Lei J X, Chen R, Yu W H, Zhang X M, Li S N, Xiang P (2005) Bone marrow-derived mesenchymal stem cells protect against experimental liver fibrosis in rats. World J Gastroenterol 11:3431-3440.

[13] Abdel Aziz M T, Atta H M, Mahfouz S, Fouad H H, Roshdy N K, Ahmed R H, Rashed L A, Sabry D, Hassouna A A, Hasan N M (2007) Therapeutic potential of bone marrow-derived mesenchymal stem cells on experimental liver fibrosis. Clin Biochem 40:893-899.

[14]Dai L J, Li H Y, Guan L X, Ritchie G, Zhou J X (2009) The therapeutic potential of bone marrow-derived mesenchymal stem cells on hepatic cirrhosis. Stem Cell Res 2:16-25.

[15]Lin S Z, Chang Y J, Liu J W, Chang L F, Sun L Y, Li Y S, Luo G H, Liao C H, Chen P H, Chen T M, Lee R P, Yang K L, Ham H J, Chiou T W (2010) Transplantation of human Wharton's Jelly-derived stem cells alleviates chemically induced liver fibrosis in rats. Cell Transplant 19:1451-1463.

What is claimed is:

1. A method for treating a liver injury in a subject comprising administering to a subject in need thereof a therapeutically effective amount of an isolated (n)-butylidenephthalide having the following formula (I) as an active ingredient, or a pharmaceutically acceptable salt or ester thereof:

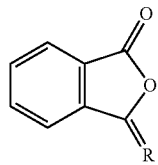
(I)

wherein R is $=CHCH_2CH_2CH_3$, and n-butylidenephthalide (I) is E form, Z form or a mixture thereof, the liver injury being liver fibrosis or liver cirrhosis.

2. The method as claimed in claim 1, wherein the therapeutically effective amount is about 8 mg to about 500 mg per kilogram of body weight per day.

3. The method as claimed in claim 1, wherein the active ingredient is extracted and isolated from a plant.

4. The method as claimed in claim 3, wherein the plant is *Angelica* sinensis or *Ligusticum* chuanxiong.

5. The method as claimed in claim 1, wherein the active ingredient is administered to the subject orally, intravenously, intramuscularly, subcutaneously or in a slow release form.

6. The method as claimed in claim 1, wherein the liver injury is caused by chemical, microorganism, physical, alcoholic, viral or congenital biliary obstruction.

7. The method of claim 1, wherein the liver injury is liver fibrosis.

8. The method of claim 1, wherein the liver injury is liver cirrhosis.

9. The method of claim 5, wherein the active ingredient is administered to the subject orally.

10. The method of claim 7, wherein the isolated (n)-butylidenephthalide is the sole active ingredient.

11. The method of claim 8, wherein the isolated (n)-butylidenephthalide is the sole active ingredient.

\* \* \* \* \*